(12) United States Patent
Ansarinia

(10) Patent No.: US 8,394,075 B2
(45) Date of Patent: *Mar. 12, 2013

(54) STIMULATION METHOD FOR THE SPHENOPALATINE GANGLIA, SPHENOPALATINE NERVE, OR VIDIAN NERVE FOR TREATMENT OF MEDICAL CONDITIONS

(76) Inventor: Mehdi M. Ansarinia, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/307,520

(22) Filed: Nov. 30, 2011

(65) Prior Publication Data

US 2012/0071811 A1   Mar. 22, 2012

Related U.S. Application Data

(60) Continuation of application No. 12/372,124, filed on Feb. 17, 2009, now Pat. No. 8,206,369, which is a division of application No. 10/245,896, filed on Sep. 17, 2002, now abandoned, which is a division of application No. 09/595,784, filed on Jun. 16, 2000, now Pat. No. 6,526,318.

(51) Int. Cl.
*A61M 31/00* (2006.01)

(52) U.S. Cl. ............ 604/500; 604/502; 604/512; 607/3; 607/46

(58) Field of Classification Search .............. 604/20–21, 604/500–501, 502, 506, 508, 512; 607/1–3, 607/40–49
See application file for complete search history.

(56) References Cited

U.S. PATENT DOCUMENTS

| 3,923,060 | A | | 12/1975 | Ellinwood, Jr. |
| 4,886,493 | A | * | 12/1989 | Yee ............................... 604/516 |
| 5,433,739 | A | | 7/1995 | Sluijter et al. |
| 5,458,631 | A | | 10/1995 | Xavier |
| 5,540,734 | A | | 7/1996 | Zabara |
| 5,735,817 | A | | 4/1998 | Shantha |

(Continued)

FOREIGN PATENT DOCUMENTS

RU   2108 817 C1   4/1998

OTHER PUBLICATIONS

Gromova et al., "Sinusoidal Modulated Currents in Comprehensive Treatment of Children with Bronchial Asthma", *Voprosy kurortologii fizioterapii, i lechebnoi fizicheskoi kultury*, May-Jun.; (3):45-7 (1981).

(Continued)

*Primary Examiner* — Theodore Stigell
(74) *Attorney, Agent, or Firm* — Tarolli, Sundheim, Covell & Tummino LLP

(57) ABSTRACT

A method is provided for suppressing or preventing pain in a patient. One step of the method includes positioning first and second electrodes, without penetrating the cranium, on or proximate to at least one of the sphenopalatine ganglia, the sphenopalatine nerves, or the vidian nerves on both sides of the patient's face. At least one of a medication solution, an analgesic, or an electrical signal is then applied to at least one of the sphenopalatine ganglia, the sphenopalatine nerves, or the vidian nerves through the first and second electrodes. Pain signal generation in, or transmission through, the at least one of the sphenopalatine ganglia, sphenopalatine nerves, or vidian nerves is disrupted on both sides of the patient's face.

8 Claims, 1 Drawing Sheet

U.S. PATENT DOCUMENTS

| | | | |
|---|---|---|---|
| 5,766,605 A | 6/1998 | Sanders et al. | |
| 6,094,598 A | 7/2000 | Elsberry et al. | |
| 6,491,940 B1 | 12/2002 | Levin | |
| 6,526,318 B1 * | 2/2003 | Ansarinia | 607/46 |
| 6,633,779 B1 | 10/2003 | Schuler et al. | |
| 6,735,475 B1 | 5/2004 | Whitehurst et al. | |
| 7,120,489 B2 | 10/2006 | Shalev et al. | |
| 7,190,998 B2 * | 3/2007 | Shalev et al. | 607/3 |
| 7,285,118 B1 | 10/2007 | Lozano | |
| 8,206,369 B2 * | 6/2012 | Ansarinia | 604/500 |
| 2003/0144709 A1 | 7/2003 | Zabara et al. | |
| 2006/0293723 A1 | 12/2006 | Whitehurst et al. | |
| 2007/0083245 A1 | 4/2007 | Lamensdorf et al. | |
| 2007/0100411 A1 | 5/2007 | Bonde | |
| 2008/0103547 A1 | 5/2008 | Okun et al. | |

OTHER PUBLICATIONS

Karashurov et al., "Radio Frequency Electrostimulation of the Gangliated Cord of the Sympathetic Nerve in Patients with Bronchial Asthma", *Surgery* (*Khigurgiia*), 2000, 1:44-46.

Gudovsky et al., "Surgical Treatment of Bronchial Asthma", *Surgery* (*Khigurgiia*), 2002, 7:14-18.

Karashurov et al., "Evoluton of Surgical Treatment of Bronchial Asthma", *Surgery* (*Khigurgiia*), 1999, 11:57-60.

* cited by examiner

STIMULATION METHOD FOR THE SPHENOPALATINE GANGLIA, SPHENOPALATINE NERVE, OR VIDIAN NERVE FOR TREATMENT OF MEDICAL CONDITIONS

CROSS REFERENCES TO RELATED APPLICATIONS

The following application is a continuation of U.S. patent application Ser. No. 12/372,124, filed Feb. 17, 2009, now U.S. Pat. No. 8,206,369 which is a divisional application of U.S. patent application Ser. No. 10/245,896, filed Sep. 17, 2002 (Now Abandoned), which is a divisional application of application Ser. No. 09/595,784 filed Jun. 16, 2000 now U.S. Pat. No. 6,526,318, issued Feb. 25, 2003. The following continuation application claims priority to the aforementioned applications for all purposes and incorporates the aforementioned applications by reference in their entireties for all purposes.

FIELD OF THE INVENTION

The present invention relates generally to methods for suppressing or preventing medical conditions such as pain, movement disorders, sleep disorders, autonomic disorders, gastrointestinal disorders, and abnormal metabolic states arising from signals generated by or transmitted through the sphenopalatine ganglia, the sphenopalatine nerve, or vidian nerve.

BACKGROUND OF THE INVENTION

Headaches are one of the most common ailments, and afflict millions of individuals. The specific etiology of headaches may be difficult to pinpoint. Known sources of headache pain include trauma and vascular, autoimmune, degenerative, infectious, drug and medication-induced, inflammatory (sarcoid), neoplastic (primary or metastatic), metabolic-endocrine, iatrogenic (such as post-surgical), muscloskelatal and myofascial causes. Even if the condition underlying the headache pain is identified and treated, headache pain may persist.

Diagnosis of headache pain will typically include an identification of one or more categories of headaches. There are a variety of different headaches with different features. Migraine headaches, as defined by the International Headache Society (IHS) Classification, are typically unilateral, throbbing headaches lasting from four to seventy-two hours. Migraines are often accompanied by nausea, vomiting, light sensitivity and/or noise sensitivity. Females suffer from migraines more than males by an approximate ratio of 3:1. Migraine headaches can be further subdivided and sub-classified into a number of different categories, such as, for example, migraine with aura, migraine without aura, and retinal migraine.

Migraines have traditionally been treated with medications to prevent their recurrence and to alleviate acute pain and associated symptoms, such as nausea and vomiting. Non-invasive modalities of migraine treatment, which may be used alone or in combination, have included: diet modification, which may include the avoidance of known headache triggers (such as certain foods); biofeedback and relaxation techniques as well as other psychological modalities; acupuncture; chiropractic manipulation; and physical therapy. Invasive therapeutic procedures have also been implemented, and have included localized anesthetic blocks as well as neurosurgical interventions, such as nerve and ganglion transections and/or resections. Unfortunately, the effectiveness of each therapeutic modality typically varies widely between individual migraine sufferers, and irrespective of the treatment modality used, the suppression of migraine pain is often short-lived, with the pain recurring at levels which are typically less but sometimes equally or rarely more intense than before treatment.

Newer techniques for treating a variety of neurological disorders have included electrical stimulation of cranial nerves of the central nervous system, such as the glossopharyngeal, vagus, or trigeminal nerves. For example, U.S. Pat. No. 5,540,734 to Zabara describes a suggested therapeutic modality for a variety of medical, psychiatric and neurological disorders, including migraines, in which modulating electrical signals are applied to either or both of the trigeminal and glossopharyngeal nerves using electrodes. The principle behind these approaches is to disrupt or modulate abnormal neuronal transmissions in the nervous system through the application of the modulating electrical signals.

Cluster headaches are so termed due to their repeated occurrence in groups or clusters. Cluster headaches are much less common than migraines: migraine sufferers outnumber cluster headache sufferers by a ratio of approximately 100:1. Cluster headaches are characterized by intense, stabbing pain usually starting in the region of an eye or temple and localizing to one side of the face. Autonomic features such as lacrimation, nasal congestion, ptosis, conjunctival injection and pupillary changes are common in cluster headaches, which occur predominantly (approximately 90%) in males and usually start in the third or fourth decade of life. It is believed that the ingestion of alcohol may trigger the onset of cluster headaches.

IHS criteria indicate that episodic attacks of cluster headaches may last up to 90 minutes and may occur as many as six times per day. Cluster headaches typically occur in cycles lasting weeks to months and then spontaneously remit. Frequently, cluster headaches have a seasonal correlation, with their onset occurring more often in the fall and spring. While there are wide variations in the start of cluster headache cycles between headache sufferers, the cycles experienced by individual headache sufferers frequently follow a defined pattern with little deviation. The headaches usually occur night, and often awaken the headache sufferer from sleep. It is not unusual for individual headache sufferers to experience the onset of cluster headaches at the same time during the night over repeated nights.

Because of the typically short duration of cluster headaches, therapies designed to abort the pain of an acute attack must have a quick onset of action. Such therapies have included oxygen inhalation, and injections of medication, such as dihydro ergotamine (DHE), ketorolac, or sumatriptan. Non-invasive therapies used to treat cluster headache pain and prevent their recurrence have included use of medications including ergot derivatives, varapamil, lithium, steroids, and sodium valproate; psychological intervention with biofeedback and relaxation techniques; and acupuncture. Anesthetic agents (such as Lidocaine) have been applied to the sphenopalatine ganglia, either directly, using a syringe, or indirectly, by soaking a long cotton swab in the anesthetic and placing the swab intranasally adjacent to the sphenopalatine ganglia, such that the anesthetic diffuses through the nasal mucosa to affect the SPG. Invasive approaches for the treatment of cluster headaches have included localized anesthetic block, surgical resection, radiofrequency, alcohol/phenol infiltration, radiosurgery and cryotherapy of the sphenopalatine ganglia and the trigeminal nerve and ganglion. The invasive approaches for treating cluster headaches are typically used only in headache sufferers who cannot tolerate the non-invasive methods of treatment, or in whom the cluster headaches are refractory and inadequately controlled with non-invasive methods.

Neuralgias, such as trigeminal, sphenopalatine, and occipital neuralgias, may start at any age, although trigeminal neuralgia is more common among the elderly. From a pathophysiological standpoint, pain arising due to neuralgias always originates from and is transmitted by the involved nerve. Accordingly, neuralgias may be caused by direct injury to nerves in the form of trauma, infection (such as herpes), neuroma formation or demyelination. Pain arising due to neuralgia may be brief and paroxysmal or continuous, and numerous attacks may occur throughout the day. Neuralgias do not feature seasonal or diurnal patterns in the onset of pain. In contrast to cluster headaches, trigeminal neuralgia often has an associated "trigger zone" on the face which can trigger the onset of the pain. Sphenopalatine neuralgia often has autonomic features, which are not commonly found in other neuralgias. In occipital neuralgia, the occipital nerve is usually tender to palpation and pain can be manifested anywhere along the course of the nerve.

Neuralgias, like migraines, have been treated using medication, invasive procedures, and, rarely, electrical stimulation of cranial nerves which are part of the central nervous system. None of the medications used in treating neuralgias have generally been effective in treating cluster headaches, other than sodium valproate.

The use of medications to treat the above-described conditions can result in systemic side-effects of wide-ranging severity. Invasive techniques used to destroy tissues, such as lesioning, resecting, freezing, or burning, are typically non-reversible, and the treatment cannot be adjusted once applied. Destruction of the tissue may itself lead to significant side effects, such as deafferentation pain.

A primary object of the present invention is to provide a method for preventing or substantially suppressing pain and other medical conditions without requiring the use of medications or destruction of nerves or other tissues in the body.

A further object of the present invention is to provide a method for preventing or substantially suppressing pain and other medical conditions which can be utilized multiple times without successive invasive procedures.

Another object of the present invention is to provide a method for preventing or substantially suppressing pain and other medical conditions which can be adjusted to the patient's individual needs without requiring further surgical intervention.

A yet further object of the present invention is to provide a method for preventing or substantially suppressing pain and other medical conditions which can be triggered and adjusted by the patient over successive uses.

Other objects and advantages of the current invention will become apparent when the inventive stimulation method is considered in conjunction with the accompanying drawings, specification and claims.

SUMMARY OF THE INVENTION

A method is provided for the suppression or prevention of pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient. The method comprises positioning at least one electrode on or proximate to at least one of the patient's sphenopalatine ganglia, sphenopalatine nerves, or vidian nerves, and activating the at least one electrode to apply an electrical signal to at least one of those ganglia or nerves.

In a further embodiment of the invention used to treat the same conditions, the electrode used is capable of being activated to dispense a medication solution or analgesic to at least one of the sphenopalatine ganglia, sphenopalatine nerves, or vidian nerves.

A method is also provided for surgically implanting an electrode on or proximate to at least one of the sphenopalatine ganglia, sphenopalatine nerves, or vidian nerves of a patient. The surgical method comprises making a first incision over the anterior portion of a coronoid notch of the patient and inserting an electrode introducer needle containing a stylet into the first incision. The electrode introducer needle is then advanced in the direction of a point one-third of the vertical distance between the flares and the nasion of the patient until the needle is about to encounter the lateral pterygoid plate of the patient. The electrode introducer needle is then advanced anteriorly until the electrode introducer needle enters the pterygopalatine fossa. The electrode introducer needle is advanced further into the pterygopalatine fossa on a trajectory bringing the electrode introducer needle as close as possible to the Vidian canal. The stylet is then removed from the electrode introducer needle, and the electrode is placed in a central channel of the electrode introducer needle. The electrode is then advanced to a distal tip of the electrode introducer needle such that the electrode is placed on or proximate to at least one of the sphenopalatine ganglia, sphenopalatine nerves, or vidian nerves of a patient; at which point the electrode introducer needle is withdrawn without displacing the electrode from its position.

BRIEF DESCRIPTION OF TEE DRAWINGS

DESCRIPTION OF THE PREFERRED EMBODIMENT

Figure 1:
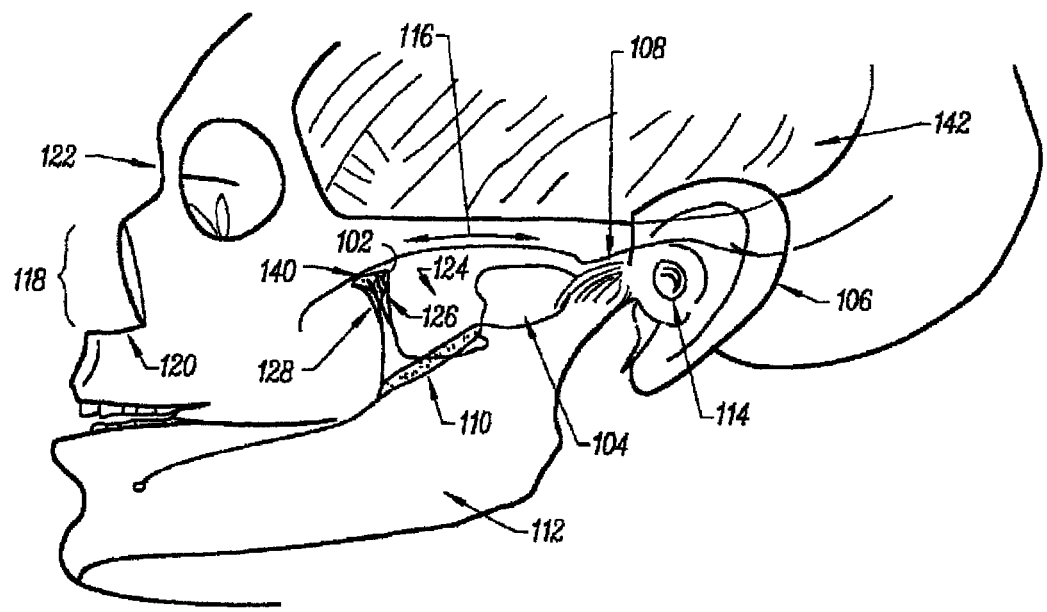
FIG. 1 is a schematic drawing of a lateral view of the skull showing the position of the infratemporal fossa with the sphenopalatine ganglion lying within the sphenopalatine fossa, surrounded by the anterior margin of the lateral pterygoid plate and the posterior wall of the maxillary sinus.

A first preferred embodiment of the inventive method utilizes direct and localized electrical stimulation of the sphenopalatine ganglion ("SPG"; also called the pterygopalatine ganglion), the sphenopalatine nerve ("SPN"; also called the pterygopalatine nerve) and/or the nerve of the pterygoid canal, also termed the vidian nerve ("VN"), using one or more surgically implanted electrodes, for treatment of a number of medical conditions. Medical conditions which may be treated by the inventive method include, but are not limited to: pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders.

Pain treatable by the inventive method may be caused by conditions including, but not limited to: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebro-spinal fluid pressure headache; temporomandibular joint disorder; atypical facial pain; ciliary neuralgia; paratrigeminal neuralgia (sometimes also termed Raeder's syndrome); petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above.

Movement disorders treatable by the inventive method may be caused by conditions including, but not limited to: Parkinson's disease; cerebropalsy; dystonia; essential tremor; and hemifacial spasms. Epilepsy treatable by the inventive method may be, for example, generalized or partial. Cerebrovascular disease treatable by the inventive method may be caused by conditions including, but not limited to: aneurysms, strokes, and cerebral hemorrhage. Autoimmune diseases treatable by the inventive method include, but are not limited to, multiple sclerosis. Sleep disorders treatable by the inventive method may be caused by conditions including, but not limited to: sleep apnea and parasomnias. Autonomic disorders treatable by the inventive method may be caused by conditions including, but not limited to: gastrointestinal disorders, including but not limited to gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease. Urinary bladder disorders treatable by the inventive method may be caused by conditions including, but not limited to: spastic or flaccid bladder. Abnormal metabolic states treatable by the inventive method may be caused by conditions including, but not limited to: hyperthyroidism or hypothyroidism. Disorders of the muscular system treatable by the inventive method include, but are not limited to, muscular dystrophy and spasms of the upper respiratory tract and face. Neuropsychiatric disorders treatable by the inventive method may be caused by conditions including, but not limited to: depression, schizophrenia, bipolar disorder, and obsessive-compulsive disorder.

The inventive method acts to suppress or prevent these conditions by disrupting sensory signals passing through the autonomic nervous system, including pain signals, as the signals traverse or are generated in the SPG, the SPN, or VN. The abnormal regulation of pain pathways, which may be a feature of the conditions described as examples above, can cause excitation or a loss of inhibition of those pathways, resulting in an increased perception of pain. Direct electrical stimulation of the SPG, SPN, and/or VN can block the transmission of pain signals and stimulate inhibitory feedback of the pain pathways passing through the SPG, SPN, and/or VN, reducing or eliminating the pain experienced by the patient. Similarly, stimulation of the SPG, SPN, and/or VN can block the transmission of signals other than pain which can provoke or aggravate other undesirable sensations or conditions, such as nausea, bladder disorders, sleep disorders or abnormal metabolic states.

The autonomic system, which innervates pain pathways within the human body, consists of two divisions: the sympathetic and the parasympathetic systems. The sympathetic and parasympathetic systems are antagonistic in their action, balancing the other system's effects within the body. The sympathetic system usually initiates activity within the body, preparing the body for action, while the parasympathetic system primarily counteracts the effects of the sympathetic system.

Figure 2:
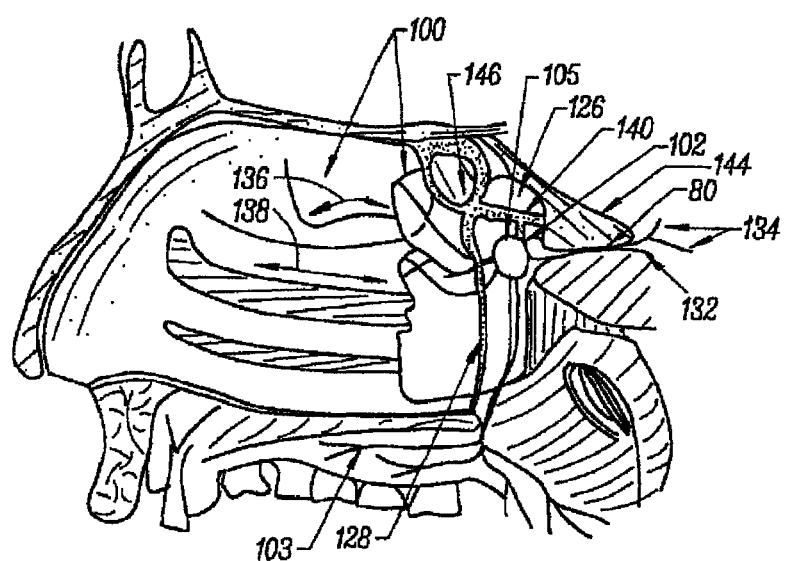
FIG. 2 is a schematic diagram of a lateral view of the lateral nasal wall showing the position of the sphenopalatine ganglion directly underneath the nasal mucosa and located at the posterior margin of the superior and middle nasal turbinates.

SPG, SPN, and VN structures are located on both sides of a patient's head. The inventive method may be applied to apply stimulus to the SPG, SPN, and/or VN on either or both sides of the patient's head. With reference to FIGS. 1 and 2, it shall be assumed for the following discussion that the inventive method is being applied to the patient's left side.

Referring to FIG. 2, the SPG 102 is located behind the maxilla 103 in the pterygopalatine fossa 126 posterior to the middle nasal turbinate 138. The SPG 102 is surrounded by a layer of mucosal and connective tissue of less than five millimeters in thickness. The SPG is part of the parasympathetic division of the autonomic nervous system. However, the SPG has both sympathetic and parasympathetic nerve fibers, as well as sensory and visceral nerve fibers. The parasympathetic activity of the SPG is mediated through the greater petrosal nerve, while the sympathetic activity of the SPG is mediated through the deep petrosal nerve, which is essentially an extension of the cervical sympathetic chain. Sensations generated by or transmitted through the SPG include, but are not limited to, sensations to the upper teeth, feelings of foreign bodies in the throat, and persistent itching of the ear. Facial nerve and carotid plexuses directly communicate sensory signals to the SPG, and cell bodies in the ventral horn of the thoracolumbar spinal cord send fibers either directly or via cervical ganglion to the SPG. The SPG transmits sensory information, including pain, to the trigeminal system via the maxillary branch.

The deep and greater petrosal nerves 134 join together just before entering the pterygoid canal to form the VN 132. The VN 132 is housed within the Vidian canal 130, which is directly posterior to the SPG 102. The VN 132 connects to the SPG 102 and contains parasympathetic fibers which synapse in the SPG 102, sensory fibers which provide sensation to part of the nasal septum, and also sympathetic fibers.

The SPN 105 are sensory nerves that connect the SPG 102 to the maxillary nerve. The SPN 105 traverse through the SPG 102 without synapsing and proceed to provide sensation to the palate. The SPN 105 suspend the SPG 102 in the pterygopalatine fossa.

Stimulation of the VN 132 and SPN 105 similarly may be used to suppress or prevent undesirable medical conditions by disrupting signals passing through the VN 132, most of which also pass through the SPG 102 due to the interconnections between the VN 132 and SPG 102.

In the preferred embodiment of the invention, one or more electrodes are surgically implanted directly on or adjacent to the SPG 102, SPN 105, and/or on the VN 132 of a patient. For purposes of clarity, in the following discussion it shall be assumed that a single electrode is implanted within the patient. However, it should be understood that multiple electrodes may be implanted according to the inventive method, and that the characteristics discussed with respect to the single electrode apply equally to additional electrodes utilized.

The electrode is preferably controllable to produce output stimulating signals which can be varied in voltage, frequency, pulse width, current, and intensity. Further, the electrode is also preferably controllable such that the controller may produce both positive and negative current flow from the electrode, stop current flow from the electrode, or change the direction of current flow from the electrode. The electrode preferably also has the capacity for variable output, linear output, and short pulse width. The electrode should be anchored securely at the site of implantation within the patient so that the output signals produced by the electrode will consistently stimulate the same regions of the SPG, SPN, and/or VN. Electrodes suitable for this purpose are produced by Medtronics Corporation under the trade name Pisces Compact.

It is recommended that the application of stimulus from the electrode and adjustments of the electrode parameters as described above will be done under the supervision and guidance of a physician. However, it should be understood that the inventive method may be applied such that the patient could, on the patient's initiative, activate the electrode to stimulate the SPG, SPN, or VN. While it may be possible to configure the electrode and its controller such that the patient could alter the parameters of the electrode stimulus without supervision by a physician, this would not be recommended as the patient may not have sufficient knowledge to avoid dangers associated with misapplication of the Inventive method.

The electrode will be connected to a power source (such as a battery or pulse generator) which provides the energy source for the electrical stimulation. The power source may be a battery implanted on or adjacent to the electrode, or the power source may be implanted at a remote site on the head or body away from the site of the electrical stimulation, as is currently done for power supplies for cardiac pacemakers and deep brain stimulators. The electrode is then connected to the remotely placed battery using wires. However, it should be understood that future technologies may be employed to provide alternative power sources. For example, it may become possible to obtain the energy needed to power the electrode directly from living tissues surrounding the electrode, such as nervous tissues, bony tissues, or fibrous tissues.

When the electrode is activated, the output of the electrode is directly applied to the SPG, SPN and/or VN, and acts to suppress the pain experienced by the patient by "blocking" the SPG, SPN or VN, respectively. As used herein, the terms "block", "blocking," and "blockade" refer to the disruption, modulation and inhibition of nerve impulse transmissions. As unregulated and increased nerve transmission is essential for the body to propagate and recognize pain, by blocking nerve impulse transmissions through the SPG, SPN, and/or VN, the inventive method can diminish the pain experienced by the patient.

As the exact parameters of the signal stimulation which may be most effective for a particular patient may vary, in the preferred embodiment the electrode is controllable such that the electrode signal can be remotely adjusted to desired settings, so that no retrieval of the electrode from the patient is necessary to adjust the patient's therapy. Remote control of the electrode output can be effected, for example, using either conventional telemetry with an implanted electrical signal generator and battery or using an implanted radiofrequency receiver coupled to an external transmitter. It should be understood that as related technologies advance, other modalities for remote control of the electrode may be employed to adjust and modulate the electrode's parameters.

The electrode may be mono-polar, bipolar, or multi-polar. However, it is preferred that a multi-polar electrode be used as lower current levels are needed to stimulate the tissue. The electrode and, if desired, any casing housing the electrode, are preferably made of inert materials (such as, for example, silicon, metal, or plastic), to reduce the risk of triggering an immune response by the patient to the implanted materials.

When stimulation is to be applied, the electrode is controlled to produce an electronic current wave. Preferably, the current wave will comprise relatively high frequency pulses with a low frequency amplitude modulation. While the exact parameters for the electrical stimulation are not yet known and are likely to vary by patient, based upon data known for stimulations performed on the brain, spinal cord, and cranial nerves, optimal settings for stimulation of the SPG, SPN, and/or VN may fall in the range of an intensity of about 0.1-20 volts, a frequency of about 1-1000 Hertz, and a pulse width of about 25-1000 microseconds. Additionally, it may be effective to produce high frequency bursts of current on top of an underlying low frequency continuous stimulus.

A variety of methods may be used to surgically implant the electrode on or adjacent to the SPG, the VN, or the SPN. Because the SPG, VN, and SPN are in very close proximity to one another within a very small area, the same technique is generally applied to achieve placement of the electrode on or adjacent to any of the three structures. Accordingly, for purposes of the following discussion, it shall be assumed that the inventive method of surgical implantation is being used to implant the electrode on or adjacent to the SPG, except where specific details are provided where applicable for use of the implantation method to implant the electrode on or adjacent to the SPN or VN. It should also be understood that, because the region in which the SPG, VN, and SPN all join together is very small, stimulation of the SPG, VN, or SPN even when the electrode is placed optimally may also stimulate one or both of the other structure.

The inventive method of surgical implantation preferably involves localization of the SPG, positioning the electrode on or adjacent to the SPG, and attaching the electrode to a power source. However, with regard to attaching the electrode to a power source, it should be understood that electrodes may be developed which make the implantation and/or attachment of a separate power source unnecessary. For example, an electrode may be used which contains its own power source, which is capable of obtaining sufficient power for operation from surrounding tissues in the patient's body, or which can be powered by bringing a power source external to the patient's body into contact with the patient's skin, such as at the cheek. In that case, the surgical procedure may be completed upon implantation of the electrode on or adjacent to the SPG.

Electrodes suitable for use with the inventive method include, but are not limited to, a multipolar electrode which is approximately 1.3 millimeters in diameter and has 4 exposed cylindrical electrical contacts approximately 1.5 millimeters in length, with a 0.5 millimeter interstice between contacts. The multipolar electrode will thus yield a total of 7.5 millimeters of distal lead length that can be employed to selectively stimulate the SPG (or SPN or VN, if applicable).

An electrode introducer needle is used to implant the electrode on or proximate to the SPG. A preferred electrode introducer needle is a 22-gauge needle which is 10 cm long and has a stylet. As an example, such an electrode introducer needle is available from Radionics in the Sluyter-Mehta kit as SMK 100 mm 2 mm active tip cannula. However, it should be understood that other electrode introducer needles may be used as appropriate to the needs and skill level of the practitioner performing the surgical procedure. For example, a needle with a smaller diameter, such as a 12-gauge, 14-gauge, 16-gauge, 18-gauge, or 20-gauge needle, may be used depending upon the diameter of the electrode to be implanted; however, the smaller diameter needles may be more difficult to manipulate and thus may require a greater skill level on the part of the practitioner.

At least one scanning apparatus, such as a CT scan or fluoroscope is preferably used to monitor the surgical procedure during the localization of the SPG. For clarity, the preferred method will be described here using a fluoroscope, but it should be understood that the method can be readily adapted for use with a CT scan. The patient is placed supine on a fluoroscopy table, with the patient's nose pointing vertically. The head is then fixed in place on the fluoroscopy table using, for example, a strip of adhesive tape. The fluoroscope (which may be, for example, a fluoroscopy c-arm unit) is then adjusted to a straight lateral position. Referring to FIG. 1, in the lateral position, the sphenopalatine fossa 126 appears as a wedge-shaped structure situated at the tip of the petrous bone 144 just inferior to the anterior aspect of the sphenoid sinus 146. The x-ray beam of the fluoroscope should then be directed towards the sphenopalatine fossa 126. The SPG 102 is situated deep in the sphenopalatine fossa 126. A marker and a metal ruler are then used to draw a line on the patient's skin over the sphenopalatine fossa 126. The entry point for the insertion of the electrode is defined by the intersection of that line with the inferior edge of the zygomatic arch 116.

This entry point for the insertion of the electrode is located in the coronoid notch 104 between the condylar 108 and coronoid processes 110 of the ramus of the mandible 112. Accordingly, as an alternative or additional method for identifying the entry point, the coronoid notch 104 may be localized by having the patient open the mouth wide and palpating the mandibular condyle (which is just anterior and inferior to the external auditory canal 114) as the mandibular condyle moves anteriorly away from the external auditory metus. When the patient then closes the mouth, the mandibular condyle will move back into place, leaving the entry point into the pterygopalatine fossa 126 (see also FIG. 2) through the coronoid notch 104 clear.

Once the entry point is localized, the skin overlying the entry point is shaved and prepared with antiseptic solution. A 25-gauge needle is used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced between the coronoid process 110 and the condylar process 108 of the ramus of the mandible 112 towards the sphenopalatine fossa 126. The electrode introducer needle is slowly advanced in the medial fashion perpendicular to the skin in the anterior-posterior (transverse) plane along the direction of the x-ray beam of the fluoroscope until it enters the sphenopalatine fossa 126.

The electrode introducer needle is then advanced further into the pterygopalatine fossa 126, at which time it will make contact with the maxillary nerve 140. The patient, upon contact, may report sharp, shooting pain and/or parasthesias in the maxilla 146. Preferably, at this point an anesthetic solution (such as, for example, 0.5 to 1 cc of 1 to 2% zylocaine or lidocaine) is administered through the electrode introducer needle to anesthetize the maxillary nerve 140 so that the electrode introducer needle can be advanced further into the sphenopalatine fossa 126 without producing significant pain in the patient.

The fluoroscope is then adjusted to an anterior-posterior position. The electrode introducer needle is advanced further in a medial fashion until it is just adjacent to the lateral aspect of the nasal cavity. The electrode introducer needle should be advanced 1 to 2 mm at a time until it just slips into the sphenopalatine foraminal opening within the lateral aspect of the nasal cavity. The electrode introducer needle must remain lateral to the nasal mucosa. The fluoroscopic images produced by the fluoroscope should be consulted frequently during this procedure to monitor the course of the electrode introducer needle.

If, during this procedure, the electrode introducer needle contacts bone, the needle should be repositioned until it moves into the sphenopalatine foraminal opening. Usually, this will be accomplished by moving the electrode introducer needle into a more superior and anterior position.

If, during the procedure, the needle is about to pierce the nasal mucosa between the superior 136 and middle 138 nasal turbinates, the needle will bulge medially into the nasopharynx, indicating that further advancing the needle may pierce the nasal mucosa. If desired, a nasal endoscope can be used in combination with the fluoroscope to show the exact placement of the lateral nasal mucosal wall in order to ensure that the nasal mucosa is not pierced by the electrode introducer needle, in order to preserve the sterility of the surgical procedure.

Once the electrode introducer needle has been positioned in the sphenopalatine foraminal opening, if it is desired to place the electrode on or adjacent to the SPN 105, the needle should be further directed to a slightly superior position. If it is desired to place the electrode on or adjacent to the VN 132, the needle should be directed slightly posteriorly to the opening of the Vidian canal 130. Although the resolution of the fluoroscopy may be limited, it may be used to verify the positioning of the needle on or proximate to the SPG 102, SPN 105 or VN 132. In this regard, a CT-scan with very thin slices may offer a higher resolution than fluoroscopy and allow more accurate exact positioning of the needle on or adjacent to the SPG 102, SPN 105 or VN 132.

Once the needle is positioned according to whether implantation is desired on or adjacent the SPG 102, SPN 105 or VN 132, the stylet is withdrawn from the electrode introducer needle. An electrode used to test the placement of the electrode introducer needle is then placed within the central channel of the needle. The electrode is then advanced to the distal tip of the needle to place the electrode on or proximate to the desired structure.

Preferably, the electrode used to test the placement of the electrode introducer needle is a radiofrequency stimulating electrode suitable to electrically stimulate the tissue at the end of the tip of the electrode and verify its position physiologically within the patient, which may be a different electrode than that ultimately implanted within the patient. A suitable radiofrequency stimulating electrode will be 10 cm with a 2-mm non-insulated active tip. The electrode should fit the full length of the central channel of the needle with its non-insulated active tip protruding through the tip of the needle to expose the electrical contacts. A suitable electrode is produced by Radionics as the 100 mm thermocouple electrode in the SMK kit.

Once the electrode is inserted through the electrode introducer needle with its electrical contacts exposed, it is then connected to an electrical stimulus/lesion generator for electrical stimulation. A suitable electrical stimulus/lesion generator is produced by Radionics as its RFG 3B model. The frequency of stimulation is set at 50 Hertz and the voltage is gradually increased until the patient reports tingling either in the nose or the soft palate. This tingling should occur at a voltage of less than one volt. If the patient experiences tingling, buzzing, or vibratory sensation just behind the nose, the electrode is in the region of the SPG 102. If the patient reports tingling in the soft palate, then to position the electrode on or proximate to the SPG 102, the electrode must be advanced a few millimeters to reach the SPG 102.

If it is desired that the electrode be positioned on or adjacent to the SPN, sensation in the palate is a likely indicator of correct positioning provided that the position of the electrode is medial to the maxillary nerve 140. The SPN 105 is located superiorly to the SPG 102, and to reach the SPN 105, the electrode should be placed superiorly in the sphenopalatine fossa 126.

If it is desired that the electrode be positioned on or adjacent to the VN 132, it is unlikely that palate sensation will be experienced with the electrical stimulation. The VN 132 is located in the posterior aspects of the sphenopalatine fossa 126. Accordingly, the electrode introducer needle should be placed in the sphenopalatine fossa 126 as posteriorly as possible so that it can be adjacent to the VN 132 as it emerges from the pterygoid canal.

In any case, if the patient experiences parasthesias outside the cheek and/or the upper lip or within the maxillary nerve distribution, then the maxillary nerve is being stimulated. In that case, the electrode should be repositioned more medially and inferiorly.

To reposition the electrode, it is removed from the electrode introducer needle while the needle is held in place. The stylet is replaced within the central channel of the electrode introducer needle, and the needle is slightly withdrawn and then re-advanced in the desired direction while keeping the same trajectory. Then, with the electrode introducer needle held firmly in place, the stylet is slowly withdrawn, and the electrode is replaced within the needle. The electrode is inserted through the channel of the needle and pushed all the way into the needle to insure the active tip of the electrode is extending beyond the tip of the needle. The correct positioning of the needle and the electrode is then checked again, as described above, using fluoroscopic imaging and electrical stimulation.

The process of repositioning of the electrode and retesting should be continued until the current stimulation yields parasthesia in or behind the nose at the clinically relevant stimulation settings. At this point, the electrode should be in optimal position.

If the electrode used to test the placement of the electrode introducer needle is a radiofrequency stimulating electrode different from the electrode to be implanted, the radiofrequency stimulating electrode is then carefully removed from the electrode introducer needle while then needle is held firmly in place to prevent displacement. The electrode to be implanted is then inserted through the central channel of the needle while the needle is held in place at the hub. As there is connective tissue and fascia around the SPG, it is believed that the electrode will remain in position. Once the electrode to be implanted is in position, preferably the correct positioning of the needle and the electrode is rechecked, as described above, using fluoroscopic imaging and electrical stimulation.

If the electrode used to test the placement of the electrode introducer needle is the electrode to be implanted, the electrode should be left in the final test position.

Once the implanted electrode is in place, the end of the electrode that is outside the skin is carefully held in place against the skin. The electrode introducer needle is then slowly removed, leaving the implanted electrode in place. At this point, if desired, a few small subcutaneous sutures may be placed around the electrode to hold it in the desired position. Preferably the correct positioning of the electrode is again checked using fluoroscopic imaging and electrical stimulation.

If the electrode moves upon the withdrawal of the needle, the electrode must be repositioned. To accomplish this, the electrode should be slightly withdrawn, and the electrode introducer needle should be reinserted over the electrode. The electrode is then completely removed and the stylet is placed back into the needle. This allows the needle with the stylet inside to be used for repositioning rather than using the more delicate electrode. The needle is then repositioned, as identified by fluoroscopy, the stylet is removed and the radiofrequency stimulating electrode (if used for testing; otherwise, the implanted electrode) is reintroduced into the needle. Electrical stimulation is again used to verify the optimal location of the electrode. The radiofrequency stimulating electrode is then removed and the electrode to be implanted is placed into the channel of the needle. Another attempt is then made to remove the needle completely without moving the electrode out of position.

Once the needle has been completely removed and the implanted electrode is in the final position, then the proximal part of the electrode that is coming out of the skin should be secured to the face by adhesive tape. Additionally, a small incision can be made on the face at the area the electrode exits the face. Then several subcutaneous sutures should be placed around the electrode to hold it in place. Extreme care should be taken during suturing to insure that the electrode is not damaged, kinked, or strangulated.

The distal end of the electrode is then connected to an extension wire or catheter, which is tunneled to the subclavicular area, or another region which will house the device used as a power source for the implanted electrode.

A tunneling instrument is used to create a subcutaneous "tunnel" starting at the face where the electrode exits the skin and continuing to the scalp, then the neck, and finally to the clavicular area. Tunneling instruments which may be used to make the tunnel tract include, but are not limited to, a Tuohy needle or a Portex tunneling instrument. The area to be tunneled should be marked and locally sterilized. Adhesive skin drapes may be used over the entire area of exposure to keep the region sterile. If desired, a local anesthetic solution may be injected along the tract to be tunneled, and the tunneling instrument may be held in place with forceps so that the electrode can be passed through the tunneling instrument.

The device or devices used to control or stimulate the electrode may be surgically implanted in the desired region by procedures known in the art, such as have been applied in surgical neuromodulation therapies used to treat Parkinson's disease.

If desired, the above procedure can then be repeated on the patient's other side to implant an electrode on or adjacent to the patient's opposing SPG.

In an alternative embodiment of the inventive method, an electrode may be utilized which, instead of or in addition to delivering electric stimulation to the SPG, SPN, or VN, delivers a medication solution or analgesic to the SPG, SPN, or VN. For example, an electrode may be used that has a small port at its tip which is connected to a reservoir or medication pump containing a medication solution or an analgesic such as an anesthetic solution. The medication/analgesic delivery electrode may be implanted using the same procedure described above for the electrical stimulation electrode. If desired by the patient or physician, the reservoir or medication pump may also be implanted in the patient's body, as described above for the electrical stimulus generator. For example, the reservoir or medication pump may be implanted subcutaneously but superficial to the anterior layer of the rectus sheath in the paraumbilical region of the abdomen. Preferably the electrode is controllable such that the amount of medication solution or analgesic applied, the rate at which medication solution or analgesic is applied, and the time period over which the medication solution or analgesic is applied can be adjusted.

It should be understood that the alternative method described above for stimulating the SPG, SPN, or VN, which utilizes delivery of a medication solution or analgesic from an electrode, may be used alone or in conjunction with the electrical stimulation method described for the preferred embodiment of the inventive method. For example, an electrode may be used which is capable of either producing an electrical stimulus or delivering a medication solution or analgesic. As another example, the electrical stimulation method could be applied to the SPG, SPN, and/or VN of one side of a patient's face, while the method utilizing delivery of a medication solution or analgesic could be applied to the SPG, SPN, and/or VN of the other side of the patient's face.

Although the foregoing invention has been described in some detail by way of illustration for purposes of clarity of understanding, it will be readily apparent to those of ordinary skill in the art in light of the teachings of this invention that certain changes and modifications may be made thereto without departing from the spirit or scope of the appended claims.

It is claimed:

1. A method for suppressing or preventing pain in a patient, the method comprising the steps of:
    advancing a first electrode, without penetrating the cranium, on or proximate to at least one of the sphenopalatine ganglia, the sphenopalatine nerves, or the vidian nerves on one side of the patient's face;
    advancing a second electrode, without penetrating the cranium, on or proximate to at least one of the sphenopalatine ganglia, the sphenopalatine nerves, or the vidian nerves on the other side of the patient's face;
    applying at least one of a medication solution, an analgesic, or an electrical signal to at least one of the sphenopalatine ganglia, the sphenopalatine nerves, or the vidian nerves through the first electrode;
    applying at least one of a medication solution, an analgesic, or an electrical signal to at least one of the sphenopalatine ganglia, the sphenopalatine nerves, or the vidian nerves through the second electrode;
    disrupting pain signal generation in, or transmission through, the at least one of the sphenopalatine ganglia, sphenopalatine nerves, or vidian nerves on the one side of the patient's face; and
    disrupting pain signal generation in, or transmission through, the at least one of the sphenopalatine ganglia, sphenopalatine nerves, or vidian nerves on the other side of the patient's face;
    wherein each of the first and second electrodes is advanced without penetrating the nasal cavity or the palate.

2. The method of claim 1 further comprising the step of:
    applying an electrical signal through each of the first and second electrodes.

3. The method of claim 1 further comprising the steps of:
    applying an electrical signal through the first electrode; and
    applying a medication solution or analgesic through the second electrode.

4. The method of claim 1 further comprising the step of:
    applying a medication solution or analgesic through each of the first and second electrodes.

5. The method of claim 1 further comprising the step of:
    adjusting at least one of the amount of the medication solution or the analgesic applied, the rate of applying the medication solution or the analgesic, and the time period of applying the medication solution or the analgesic.

6. The method of claim 5, the amount of the medication solution or the analgesic applied, the rate of applying the medication solution or the analgesic, and the time period of applying the medication solution or the analgesic being controllable by a reservoir or a medication pump.

7. The method of claim 1, wherein at least one of the first and second electrodes is remotely controlled using a remote control device which is accessible from outside the body of the patient.

8. The method of claim 1, wherein at least one of the first and second electrodes is powered by a power source surgically implanted within the patient.

* * * * *